United States Patent [19]

Nakamura et al.

[11] Patent Number: 5,659,016
[45] Date of Patent: Aug. 19, 1997

[54] RPDL PROTEIN AND DNA ENCODING THE SAME

[75] Inventors: Yusuke Nakamura; Yoichi Furukawa, both of Kanagawa, Japan

[73] Assignees: Cancer Institute; Eisai Co., Ltd., both of Tokyo, Japan

[21] Appl. No.: 528,255

[22] Filed: Sep. 14, 1995

[30] Foreign Application Priority Data

Sep. 22, 1994 [JP] Japan .................................. 6-227876

[51] Int. Cl.⁶ .............................. A61K 38/16; C07K 1/00; C07K 14/00; C07K 17/00
[52] U.S. Cl. ................ 530/358; 530/350; 530/387.9; 530/388.1; 530/389.1
[58] Field of Search .................... 530/350, 358, 530/387.9, 388.1, 389.1

[56] References Cited

PUBLICATIONS

Grundy et al Mol. Microbiol. vol. 10 p. 259 1993.
Mol. Cell. Biol., vol. 11, No. 12, Dec. 1991, pp. 6317–6327, Vidal. M. & Gaber, R.F. 'RPD3 encodes a second factor . . . '.
Genomics, vol. 24, No. 2, 15 Nov. 1994, pp. 276–279, Sudo, K. et al. '2058 expressed sequence tags . . . ' & DDBJ database entry HSL13977, accession No. D31480.
EMBL database entry Xlab 21, accession No. X78454, submitted 25 Mar. 1994; Ladomery, M.R. et al, "yeast RPD3 homologue from X. laevis".
Scientific American, vol. 260, Jun. 1989, pp. 40–47, Holliday, R. 'A different kind of inheritance'.

*Primary Examiner*—Toni R. Scheiner
*Assistant Examiner*—Sheela J. Huff
*Attorney, Agent, or Firm*—Flynn, Thiel, Boutell & Tanis, P.C.

[57] ABSTRACT

The 5-terminal partially nucleotide sequence of each clone of a human fetal lung tissue cDNA library was determined. A clone having a novel sequence including a sequence homologous to that of the transcriptional control protein of a yeast was selected from among the above clones and its whole nucleotide structure was determined. It was confirmed that the protein encoded by the gene of the clone was a novel human transcriptional control protein (RPDL protein). Further, an expression vector for expressing the protein and a transformant obtained by transforming with such an expression vector can also be prepared.

2 Claims, No Drawings

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 482
        ( B ) TYPE: amino acid
        ( C ) STRANDEDNESS:
        ( D ) TOPOLOGY: linear ( i i ) MOLECULE TYPE: protein ( v i ) ORIGINAL SOURCE:
        ( A ) ORGANISM: Homo sapiens ( v i i ) IMMEDIATE SOURCE:
        ( A ) LIBRARY: human fetal lung cDNA library ( x i ) SEQUENCE DESCRIPTION: SEQ ID NO: 1:

```
Met Ala Gln Thr Gln Gly Thr Arg Arg Lys Val Cys Tyr Tyr Tyr Asp
 1               5                  10                 15
Gly Asp Val Gly Asn Tyr Tyr Tyr Gly Gln Gly His Pro Met Lys Pro
                20                 25                 30
His Arg Ile Arg Met Thr His Asn Leu Leu Leu Asn Tyr Gly Leu Tyr
            35                 40                 45
Arg Lys Met Glu Ile Tyr Arg Pro His Lys Ala Asn Ala Glu Glu Met
        50                 55                 60
Thr Lys Tyr His Ser Asp Asp Tyr Ile Lys Phe Leu Arg Ser Ile Arg
 65                 70                 75                 80
Pro Asp Asn Met Ser Glu Tyr Ser Lys Gln Met Gln Arg Phe Asn Val
                85                 90                 95
Gly Glu Asp Cys Pro Val Phe Asp Gly Leu Phe Glu Phe Cys Gln Leu
               100                105                110
Ser Thr Gly Gly Ser Val Ala Ser Ala Val Lys Leu Asn Lys Gln Gln
           115                120                125
Thr Asp Ile Ala Val Asn Trp Ala Gly Gly Leu His His Ala Lys Lys
       130                135                140
Ser Glu Ala Ser Gly Phe Cys Tyr Val Asn Asp Ile Val Leu Ala Ile
145                150                155                160
Leu Glu Leu Leu Lys Tyr His Gln Arg Val Leu Tyr Ile Asp Ile Asp
               165                170                175
Ile His His Gly Asp Gly Val Glu Glu Ala Phe Tyr Thr Thr Asp Arg
           180                185                190
Val Met Thr Val Ser Phe His Lys Tyr Gly Glu Tyr Phe Pro Gly Thr
       195                200                205
Gly Asp Leu Arg Asp Ile Gly Ala Gly Lys Gly Lys Tyr Tyr Ala Val
   210                215                220
Asn Tyr Pro Leu Arg Asp Gly Ile Asp Asp Glu Ser Tyr Glu Ala Ile
225                230                235                240
Phe Lys Pro Val Met Ser Lys Val Met Glu Met Phe Gln Pro Ser Ala
               245                250                255
Val Val Leu Gln Cys Gly Ser Asp Ser Leu Ser Gly Asp Arg Leu Gly
```

|             |             |             |             |             |             |             |             |             |             |             |             |             |             |
|-------------|-------------|-------------|-------------|-------------|-------------|-------------|-------------|-------------|-------------|-------------|-------------|-------------|-------------|
|             |             |             |             |             | 260         |             |             |             |             | 265         |             |             | 270         |
| Cys | Phe | Asn | Leu | Thr | Ile | Lys | Gly | His | Ala | Lys | Cys | Val | Glu | Phe | Val |
|     | 275 |     |     |     |     | 280 |     |     |     |     | 285 |     |     |     |     |
| Lys | Ser | Phe | Asn | Leu | Pro | Met | Leu | Met | Leu | Gly | Gly | Gly | Gly | Tyr | Thr |
|     | 290 |     |     |     |     | 295 |     |     |     |     | 300 |     |     |     |     |
| Ile | Arg | Asn | Val | Ala | Arg | Cys | Arg | Thr | Tyr | Glu | Thr | Ala | Val | Ala | Leu |
| 305 |     |     |     |     | 310 |     |     |     |     | 315 |     |     |     |     | 320 |
| Asp | Thr | Glu | Ile | Pro | Asn | Glu | Leu | Pro | Tyr | Asn | Asp | Tyr | Phe | Glu | Tyr |
|     |     |     |     | 325 |     |     |     |     | 330 |     |     |     |     | 335 |     |
| Phe | Gly | Pro | Asp | Phe | Lys | Leu | His | Ile | Ser | Pro | Ser | Asn | Met | Thr | Asn |
|     |     |     | 340 |     |     |     |     | 345 |     |     |     |     | 350 |     |     |
| Gln | Asn | Thr | Asn | Glu | Tyr | Leu | Glu | Lys | Ile | Lys | Gln | Arg | Leu | Phe | Glu |
|     |     | 355 |     |     |     |     | 360 |     |     |     |     | 365 |     |     |     |
| Asn | Leu | Arg | Met | Leu | Pro | His | Ala | Pro | Gly | Val | Gln | Met | Gln | Ala | Ile |
|     | 370 |     |     |     |     | 375 |     |     |     |     | 380 |     |     |     |     |
| Pro | Glu | Asp | Ala | Ile | Pro | Glu | Glu | Ser | Gly | Asp | Glu | Asp | Glu | Asp | Asp |
| 385 |     |     |     |     | 390 |     |     |     |     | 395 |     |     |     |     | 400 |
| Pro | Asp | Lys | Arg | Ile | Ser | Ile | Cys | Ser | Ser | Asp | Lys | Arg | Ile | Ala | Cys |
|     |     |     |     | 405 |     |     |     |     | 410 |     |     |     |     | 415 |     |
| Glu | Glu | Glu | Phe | Ser | Asp | Ser | Glu | Glu | Gly | Glu | Gly | Gly | Arg | Lys |
|     |     |     | 420 |     |     |     |     | 425 |     |     |     |     | 430 |     |
| Asn | Ser | Ser | Asn | Phe | Lys | Lys | Ala | Lys | Arg | Val | Lys | Thr | Glu | Asp | Glu |
|     |     | 435 |     |     |     |     | 440 |     |     |     |     | 445 |     |     |     |
| Lys | Glu | Lys | Asp | Pro | Glu | Glu | Lys | Lys | Glu | Val | Thr | Glu | Glu | Glu | Lys |
|     | 450 |     |     |     |     | 455 |     |     |     |     | 460 |     |     |     |     |
| Thr | Lys | Glu | Glu | Lys | Pro | Glu | Ala | Lys | Gly | Val | Lys | Glu | Glu | Val | Lys |
| 465 |     |     |     |     | 470 |     |     |     |     | 475 |     |     |     |     | 480 |
| Leu | Ala |
|     | 482 |

( 2 ) INFORMATION FOR SEQ ID NO: 2:

( i ) SEQUENCE CHARACTERISTICS:
        ( A ) LENGTH: 2111
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Homo sapiens ( v i i ) IMMEDIATE SOURCE:
        ( A ) LIBRARY: human fetal lung cDNA library ( i x ) FEATURE:
        ( A ) NAME/KEY: CDS
        ( B ) LOCATION: 64..1512
        ( C ) IDENTIFICATION METHOD: experimental examination ( x i ) SEQUENCE DESCRIPTION: SEQ ID NO: 2:

```
GAGCGGAGCC  GCGGGCGGGA  GGGCGGACGG  ACCGACTGAC  GGTAGGGACG  GGAGGCGAGC         60

AAG ATG GCG CAG ACG CAG GGC ACC CGG AGG AAA GTC TGT TAC TAC TAC             108
    Met Ala Gln Thr Gln Gly Thr Arg Arg Lys Val Cys Tyr Tyr Tyr
    1               5                   10                  15

GAC GGG GAT GTT GGA AAT TAC TAT TAT GGA CAA GGC CAC CCA ATG AAG             156
Asp Gly Asp Val Gly Asn Tyr Tyr Tyr Gly Gln Gly His Pro Met Lys
                    20                  25                  30

CCT CAC CGA ATC CGC ATG ACT CAT AAT TTG CTG CTC AAC TAT GGT CTC             204
Pro His Arg Ile Arg Met Thr His Asn Leu Leu Leu Asn Tyr Gly Leu
```

|  |  |  |  |  |  |  |  |  |  |  |  |  |  |  |  |
|---|---|---|---|---|---|---|---|---|---|---|---|---|---|---|---|
|  |  | 35 |  |  |  |  | 40 |  |  |  |  | 45 |  |  |  |
| TAC | CGA | AAA | ATG | GAA | ATC | TAT | CGC | CCT | CAC | AAA | GCC | AAT | GCT | GAG | GAG |
| Tyr | Arg | Lys<br>50 | Met | Glu | Ile | Tyr | Arg<br>55 | Pro | His | Lys | Ala | Asn<br>60 | Ala | Glu | Glu |

252

ATG ACC AAG TAC CAC AGC GAT GAC TAC ATT AAA TTC TTG CGC TCC ATC    300
Met Thr Lys Tyr His Ser Asp Asp Tyr Ile Lys Phe Leu Arg Ser Ile
        65              70              75

CGT CCA GAT AAC ATG TCG GAG TAC AGC AAG CAG ATG CAG AGA TTC AAC    348
Arg Pro Asp Asn Met Ser Glu Tyr Ser Lys Gln Met Gln Arg Phe Asn
80                  85                  90                      95

GTT GGT GAG GAC TGT CCA GTA TTC GAT GGC CTG TTT GAG TTC TGT CAG    396
Val Gly Glu Asp Cys Pro Val Phe Asp Gly Leu Phe Glu Phe Cys Gln
                    100                 105                 110

TTG TCT ACT GGT GGT TCT GTG GCA AGT GCT GTG AAA CTT AAT AAG CAG    444
Leu Ser Thr Gly Gly Ser Val Ala Ser Ala Val Lys Leu Asn Lys Gln
            115                 120                 125

CAG ACG GAC ATC GCT GTG AAT TGG GCT GGG GGC CTG CAC CAT GCA AAG    492
Gln Thr Asp Ile Ala Val Asn Trp Ala Gly Gly Leu His His Ala Lys
        130             135                 140

AAG TCC GAG GCA TCT GGC TTC TGT TAC GTC AAT GAT ATC GTC TTG GCC    540
Lys Ser Glu Ala Ser Gly Phe Cys Tyr Val Asn Asp Ile Val Leu Ala
    145                 150                 155

ATC CTG GAA CTG CTA AAG TAT CAC CAG AGG GTG CTG TAC ATT GAC ATT    588
Ile Leu Glu Leu Leu Lys Tyr His Gln Arg Val Leu Tyr Ile Asp Ile
160             165                 170                     175

GAT ATT CAC CAT GGT GAC GGC GTG GAA GAG GCC TTC TAC ACC ACG GAC    636
Asp Ile His His Gly Asp Gly Val Glu Glu Ala Phe Tyr Thr Thr Asp
            180                 185                 190

CGG GTC ATG ACT GTG TCC TTT CAT AAG TAT GGA GAG TAC TTC CCA GGA    684
Arg Val Met Thr Val Ser Phe His Lys Tyr Gly Glu Tyr Phe Pro Gly
        195                 200                 205

ACT GGG GAC CTA CGG GAT ATC GGG GCT GGC AAA GGC AAG TAT TAT GCT    732
Thr Gly Asp Leu Arg Asp Ile Gly Ala Gly Lys Gly Lys Tyr Tyr Ala
    210                 215                 220

GTT AAC TAC CCG CTC CGA GAC GGG ATT GAT GAC GAG TCC TAT GAG GCC    780
Val Asn Tyr Pro Leu Arg Asp Gly Ile Asp Asp Glu Ser Tyr Glu Ala
225             230                 235

ATT TTC AAG CCG GTC ATG TCC AAA GTA ATG GAG ATG TTC CAG CCT AGT    828
Ile Phe Lys Pro Val Met Ser Lys Val Met Glu Met Phe Gln Pro Ser
240             245                 250                     255

GCG GTG GTC TTA CAG TGT GGC TCA GAC TCC CTA TCT GGG GAT CGG TTA    876
Ala Val Val Leu Gln Cys Gly Ser Asp Ser Leu Ser Gly Asp Arg Leu
            260                 265                 270

GGT TGC TTC AAT CTA ACT ATC AAA GGA CAC GCC AAG TGT GTG GAA TTT    924
Gly Cys Phe Asn Leu Thr Ile Lys Gly His Ala Lys Cys Val Glu Phe
        275                 280                 285

GTC AAG AGC TTT AAC CTG CCT ATG CTG ATG CTG GGA GGC GGT GGT TAC    972
Val Lys Ser Phe Asn Leu Pro Met Leu Met Leu Gly Gly Gly Gly Tyr
    290                 295                 300

ACC ATT CGT AAC GTT GCC CGG TGC AGG ACA TAT GAG ACA GCT GTG GCC    1020
Thr Ile Arg Asn Val Ala Arg Cys Arg Thr Tyr Glu Thr Ala Val Ala
305                 310                 315

CTG GAT ACG GAG ATC CCT AAT GAG CTT CCA TAC AAT GAC TAC TTT GAA    1068
Leu Asp Thr Glu Ile Pro Asn Glu Leu Pro Tyr Asn Asp Tyr Phe Glu
320             325                 330                     335

TAC TTT GGA CCA GAT TTC AAG CTC CAC ATC AGT CCT TCC AAT ATG ACT    1116
Tyr Phe Gly Pro Asp Phe Lys Leu His Ile Ser Pro Ser Asn Met Thr
            340                 345                 350

AAC CAG AAC ACG AAT GAG TAC CTG GAG AAG ATC AAA CAG CGA CTG TTT    1164
Asn Gln Asn Thr Asn Glu Tyr Leu Glu Lys Ile Lys Gln Arg Leu Phe

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 355 |     |     |     |     |     | 360 |     |     |     |     |     | 365 |      |
| GAG | AAC | CTT | AGA | ATG | CTG | CCG | CAC | GCA | CCT | GGG | GTC | CAA | ATG | CAG | GCG | 1212 |
| Glu | Asn | Leu | Arg | Met | Leu | Pro | His | Ala | Pro | Gly | Val | Gln | Met | Gln | Ala |      |
|     |     | 370 |     |     |     |     | 375 |     |     |     |     | 380 |     |     |     |      |
| ATT | CCT | GAG | GAC | GCC | ATC | CCT | GAG | GAG | AGT | GGC | GAT | GAG | GAC | GAA | GAC | 1260 |
| Ile | Pro | Glu | Asp | Ala | Ile | Pro | Glu | Glu | Ser | Gly | Asp | Glu | Asp | Glu | Asp |      |
|     | 385 |     |     |     |     | 390 |     |     |     |     | 395 |     |     |     |     |      |
| GAC | CCT | GAC | AAG | CGC | ATC | TCG | ATC | TGC | TCC | TCT | GAC | AAA | CGA | ATT | GCC | 1308 |
| Asp | Pro | Asp | Lys | Arg | Ile | Ser | Ile | Cys | Ser | Ser | Asp | Lys | Arg | Ile | Ala |      |
| 400 |     |     |     |     | 405 |     |     |     |     | 410 |     |     |     |     | 415 |      |
| TGT | GAG | GAA | GAG | TTC | TCC | GAT | TCT | GAA | GAG | GAG | GGA | GAG | GGG | GGC | CGC | 1356 |
| Cys | Glu | Glu | Glu | Phe | Ser | Asp | Ser | Glu | Glu | Glu | Gly | Glu | Gly | Gly | Arg |      |
|     |     |     |     | 420 |     |     |     |     | 425 |     |     |     |     | 430 |     |      |
| AAG | AAC | TCT | TCC | AAC | TTC | AAA | AAA | GCC | AAG | AGA | GTC | AAA | ACA | GAG | GAT | 1404 |
| Lys | Asn | Ser | Ser | Asn | Phe | Lys | Lys | Ala | Lys | Arg | Val | Lys | Thr | Glu | Asp |      |
|     |     | 435 |     |     |     |     |     | 440 |     |     |     |     | 445 |     |     |      |
| GAA | AAA | GAG | AAA | GAC | CCA | GAG | GAG | AAG | AAA | GAA | GTC | ACC | GAA | GAG | GAG | 1452 |
| Glu | Lys | Glu | Lys | Asp | Pro | Glu | Glu | Lys | Lys | Glu | Val | Thr | Glu | Glu | Glu |      |
|     |     | 450 |     |     |     |     | 455 |     |     |     |     | 460 |     |     |     |      |
| AAA | ACC | AAG | GAG | GAG | AAG | CCA | GAA | GCC | AAA | GGG | GTC | AAG | GAG | GAG | GTC | 1500 |
| Lys | Thr | Lys | Glu | Glu | Lys | Pro | Glu | Ala | Lys | Gly | Val | Lys | Glu | Glu | Val |      |
|     | 465 |     |     |     |     | 470 |     |     |     |     | 475 |     |     |     |     |      |
| AAG | TTG | GCC | TGAATGGACC | TCTCCAGCTC | TGGCTTCCTG | CTGAGTCCCT |     |     |     |     |     |     |     |     |     | 1549 |
| Lys | Leu | Ala |     |     |     |     |     |     |     |     |     |     |     |     |     |      |
| 480 |     | 482 |     |     |     |     |     |     |     |     |     |     |     |     |     |      |

```
CACGTTTCTT  CCCCAACCCC  TCAGATTTTA  TATTTCTAT   TTCTCTGTGT  ATTTATATAA  1609
AAATTTATTA  AATATAAATA  TCCCCAGGGA  CAGAAACCAA  GGCCCCGAGC  TCAGGGCAGC  1669
TGTGCTGGGT  GAGCTCTTCC  AGGAGCCACC  TTGCCACCCA  TTCTTCCCGT  TCTTAACTTT  1729
GAACCATAAA  GGGTGCCAGG  TCTGGGTGAA  AGGGATACTT  TTATGCAACC  ATAAGACAAA  1789
CTCCTGAAAT  GCCAAGTGCC  TGCTTAGTAG  CTTTGGAAAG  GTGCCCTTAT  TGAACATTCT  1849
AGAAGGGGTG  GCTGGGTCTT  CAAGGATCTC  CTGTTTTTTT  CAGGCTCCTA  AAGTAACATC  1909
AGCCATTTTT  AGATTGGTTC  TGTTTTCGTA  CCTTCCCACT  GGCCTCAAGT  GAGCCAAGAA  1969
ACACTGCCTG  CCCTCTGTCT  GTCTTCTCCT  AATTCTGCAG  GTGGAGGTTG  CTAGTCTAGT  2029
TTCCTTTTG   AGATACTATT  TTCATTTTTG  TGAGCCTCTT  TGTAATAAAA  TGGTACATTT  2089
CTAAAAAAAA  AAAAAAAAA   AA                                              2111
```

RPDL PROTEIN AND DNA ENCODING THE SAME

BACKGROUND OF THE INVENTION

1. Field of the Invention

The present invention relates to an RPDL protein which is a novel transcriptional control protein, a process for producing this protein, a method of using the same, a DNA encoding the protein, and a gene analysis method using the DNA. The present invention finds applications in the pharmaceutical field.

2. Description of the Related Art

Many genes execute selective expression, for example, at a specific time or site or when a certain stimulus has been given. The expression of the genes involves two important steps consisting of producing a mRNA on the basis of information stored in the DNA sequence (transcription) and producing a protein by the action of the mRNA (translation).

It is becoming apparent in recent years that the transcription of genes in eukaryotic cells is skillfully controlled by a plurality of proteins known as transcriptional control proteins.

Analyzing in detail the mechanism of the above transcriptional control is a task extremely important from the viewpoint of learning the selective expression control mechanism of genes, namely, the cell differentiation or amplification or various gene activities and ultimately the fundamental system relating to, for example, life and death. It is expected that the analysis of the mechanism of the above transcriptional control would break through difficult problems of not only tumors but also other various diseases and abnormalities, and further, aging, dementia, obesity, etc.

For the elucidation of the transcriptional control mechanism, it is essential to achieve "understanding the material bases of associated factors (transcriptional control protein, etc.)", "understanding the interaction between such factors", "understanding the whole process through a plurality of interactions", and "working out a systematic understanding through commonality and diversity" [see Masami Horikoshi et al, Tanpaku-shitsu.Kakusan.Koso (Protein, Nucleic Acid and Enzyme), Vol.38, No.5, p.p.831–841 (1993)].

Studies on structural fundamentals such that some basic transcription factors recognize specific sequences of the DNA and bind therewith have been advanced with the use of viruses, bacteria, yeasts, and the like. However, for example, the number of constituent factor groups is so large that elucidation is still being awaited in various fields such as the interaction between factors, the interaction of the factor with a component of transcription initiation complex, such as RNA polymerase, and the commonality in the control mechanism between viruses, bacteria, yeasts and human. Therefore, a marked progress of the analysis described above based on the recent gene isolations, especially, the cDNA clonings of factors associated with the human transcriptional control mechanism is being expected.

Known transcriptional control proteins include those specific for some genes and those commonly acting on a wide variety of genes. From the viewpoint of function, the known transcriptional control proteins include not only those capable of activating the transcription or inactivating the same but also those having both of the above capabilities [see M. Ptashne, Scientific American, Vol.260, p.p.40–47 (1989)].

Up to now, studies on eukaryotic cells in this field have been conducted with the use of yeast as the model from the practical point of view, and it has been suggested that the fundamental mechanism thereof applies to human cells as well. The transcriptional control protein not only commonly acting on many genes but also having both the functions of activation and inactivation is considered as being especially important and, therefore, it is apparent that the studies on the effects exerted by its mutation with the use of yeast only have reached a limit.

Accordingly, isolating a human gene encoding the above important transcriptional control protein and identifying the protein has an extremely important significance in that a marked progress can be realized in the direct elucidation of the transcriptional control mechanism of the cells of multicellular organisms having such aspects as development, differentiation and tissue, especially, human per se.

Disclosure of the Invention

SUMMARY OF THE INVENTION

An object of the present invention is to provide an important human transcriptional control protein not only commonly acting on many target genes but also having both the functions of activation and inactivation, and a gene encoding the protein. Another object of the present invention is to provide a gene analysis method useful for elucidative studies on the mechanism of control of human gene transcription and on the effects on human cells caused by the mutation of the gene encoding the human transcriptional control protein with the use of the transcriptional control protein and DNA encoding the same.

The yeast transcription factor RPD3 controls not only the transcription of high- and low-affinity potassium transporter gene TRK2 but also the transcription of many genes including genes PHO5, STE6 and TY2 as the target. Further, it is known that the yeast PRD3 protein has both the functions of activation and inactivation [see M. Vidal and R. F. Gaber, Mol. Cel. Biol. Vol.11, p.p.6317–6327 (1991)].

The present inventors have determined the 5'-terminal nucleotide sequence of each clone derived from a cDNA library prepared from human fetal lung and have found a clone exhibiting homology with the sequence of the RPD3 gene of a yeast. Further, they have determined the DNA sequence of this clone and have obtained a full-length cDNA encoding a novel protein. It has been confirmed that the amino acid sequence of the protein encoded by this cDNA exhibits a significant similarity to that of the yeast RPD3 and this protein is a novel human transcriptional control protein that has never been reported.

Moreover, the present inventors have confirmed that the gene encoding this protein is an important gene which is expressed in all the studied human tissues, excluding the brain, by a gene analysis according to the Northern blotting technique using the above cDNA as a probe.

Furthermore, the present inventors have confirmed that the gene encoding this protein is localized at 1p34.1 on the short arm of chromosome 1, the region where a deletion is recognized in mammary and gastric carcinomas, by chromosomal mapping according to the FISH (fluorescent in situ hybridization) technique using the above cDNA as a probe.

The present invention has enabled not only the production of a transformant having, introduced thereinto, the cDNA encoding the above human transcriptional control protein or a DNA obtained by artificially mutating the same by introducing the cDNA or the DNA into a host such as E. coli, yeast, an insect cell and a mammal cell, but also the production of the above protein or its variant With the use of the transformant and, further, the production of an antibody capable of binding with the above protein or its variant. Moreover, the present invention has enabled, on the level of human cells, not only the analyses of the interaction between the above protein and other factors capable of binding therewith, human genes controlled as the target and the activation and inactivation functions of the above protein as the transcriptional control factor, but also studies of the effects caused by the mutation of the DNA encoding the above protein.

Thus, the present invention provides an RPDL protein having an amino acid sequence comprising the whole or a part of the amino acid sequence specified in sequence ID NO 1, or a variant of said RPDL protein. In the above explanation, "the variant of said RPDL protein" is a RPDL protein having an amino acid sequence comprising the whole or a part of an amino acid sequence which is identical with the one specified in sequence ID NO 1 except that one or more amino acids are added thereto, deleted therefrom or inserted thereinto, or that one or more amino acids are substituted for one or more amino acids contained in sequence ID NO 1, and acts in the same manner as that of said RPDL protein having an amino acid sequence comprising the whole or a part of the amino acid sequence specified in sequence ID NO 1.

Further, the present invention provides a DNA encoding said RPDL protein or a variant of said RPDL protein; a vector which contains a DNA encoding said RPDL protein or a variant of said RPDL protein; a transformant having, introduced thereinto, said vector; a process for producing said RPDL protein or a variant of said RPDL protein, which comprises culturing said transformant and recovering an expression product thereof; and a polyclonal antibody or a monoclonal antibody capable of combining with said RPDL protein or a variant of said RPDL protein.

Furthermore, the present invention provides a DNA probe having a DNA sequence, said DNA sequence comprising the whole or a part of the DNA sequence specified in sequence ID NO 2 or comprising a sequence complementary to the whole or a part of the DNA sequence specified in sequence ID NO 2; a DNA primer having a DNA sequence, said DNA sequence comprising a part of the DNA sequence specified in sequence ID NO 2 or comprising a sequence complementary to a part of the DNA sequence specified in sequence ID NO 2; and a gene analysis method for an RPDL protein characterized by hybridizing said DNA probe or said DNA primer with a subject DNA.

In other words, the present invention relates to (1) a protein comprising the whole or a part of the protein represented by sequence ID NO 1 or a variant thereof; (2) a DNA comprising the whole or a part of the DNA represented by sequence ID NO 2 or a mutant thereof, (3) a plasmid including the above DNA and a transformant carrying the same, (4) a process for producing the above protein, (5) an antibody capable of binding with the above protein, and (6) a probe or primer including a part of the above DNA sequence and a gene analysis method or gene amplification method characterized by using the same.

The present invention will be described in detail below.

DETAILED DESCRIPTION OF THE INVENTION (1) Isolation of cDNA clone and confirmation of nucleotide sequence and amino acid sequence cDNA was synthesized on the basis of mRNA derived from human fetal lung tissue and a cDNA library containing cloned cDNA inserts in a given direction was prepared. The nucleotide sequence of each clone of this library was determined partially from the 5'-terminal side and one clone having a nucleotide sequence homologous with the RPD3 gene of a yeast was obtained. Further, the whole nucleotide sequence of this clone was determined with the result that the desired full-length cDNA sequence was obtained.

The cDNA obtained by the above procedure was confirmed as having a novel DNA sequence represented by sequence ID NO 2 and the amino acid sequence of a novel protein encoded thereby was deduced as shown in sequence ID NO 1. The present inventors designated the protein having the sequence specified in sequence ID NO 1 as a RPDL protein, this designation being employed throughout this description.

The DNA of the present invention and a DNA complementary to said DNA can find applications in gene and gene expression analyses by the use of a part thereof as a primer or probe. The term "a part of the DNA" as used herein means a continuous sequence of at least six nucleotides, preferably, at least eight nucleotides, still more preferably, at least ten nucleotides, and most preferably 10 to 12 nucleotides or 15 to 25 nucleotides corresponding to (i.e., contained in or complementary to) the nucleotide sequence of the DNA according to the present invention. The primer or probe of the present invention which is an oligonucleotide or polynucleotide may contain also at least one nucleotide(s) not corresponding to the nucleotide sequence of the DNA encoding the RPDL protein.

The protein of the present invention can find applications in antibody preparation and agents for study and diagnostics containing such antibodies by the use of the whole or a part thereof as an epitope. The term "epitope" means an antigenic determinant of a polypeptide. It is well known that the epitope is generally composed of at least 5 amino acid residues and that a polypeptide composed of 6 amino acid residues combines with an antibody [see WO of PCT Patent Applications No. 8403564, published on Sep. 13, 1984 (Assignee: COMMONWEALTH SERUM LABS AND GEYSEN, H.M.)]. The term "a part of the protein" as used herein refers to a polypeptide comprising at least about 3 to 5 consecutive amino acid residues, preferably at least about 8 to 10 consecutive amino acid residues, and still more preferably, at least about 11 to 20 consecutive amino acid residues, on the basis of the amino acid sequence of the protein of the present invention. Needless to say, use can be made of even a polypeptide comprising at least about 20 amino acid residues. The polypeptide described above may contain also at least one amino acid residues not corresponding to the amino acid sequence of the RPDL protein.

The present invention comprehends RPDL proteins which are substantially equivalent to the RPDL protein having an amino acid sequence specified in sequence ID NO 1 and which are obtained by addition, deletion, insertion or substitution of one or more constituent amino acid residues of the above protein. Such equivalents are included in the present invention as long as they exert similar effects in the study and diagnosis regarding the RPDL protein. As in the protein above, DNAs which are substantially equivalent to the DNA encoding the RPDL protein having an amino acid sequence specified in sequence ID NO 1 and which are obtained by addition, deletion, insertion or substitution of one or more constituent nucleotides of the above DNA, i.e., equivalents, are also included in the present invention.

(2) Recombinant expression vector and preparation of transformant and protein

A transformant can be obtained by inserting the DNA of the present invention or a part thereof into a suitable vector and transfecting this vector into suitable host cells. Human RPDL protein or a part thereof can be produced in a large quantity by culturing the transformant in the customary manner and separating it from the resultant culture. More particularly, a recombinant expression vector can be prepared by religating the above DNA or a fragment thereof to a vector suitable for the expression downstream of the promoter according to the customary procedure in which a restriction enzyme and DNA ligase are employed. Examples of suitable vectors include plasmids pBR322 and pUC18 derived from *Escherichia coli*, plasmid pUB110 derived from *Bacillus subtilis*, plasmid pRB15 derived from yeast, bacteriophage vectors λgt10 and λgt11, and vector SV40. The vectors are not particularly limited as long as they can be replicated or amplified in the host. The promoter and terminator are also not particularly limited as long as they suit the host employed in the expression of the DNA sequence. Appropriate members thereof can be used in combination in accordance with the host. The DNA to be employed is not limited to a one having a DNA sequence specified in sequence ID NO 2. Use may be made of a DNA having a DNA sequence resulting from intentional or unintentional substitution, deletion, insertion and/or addition conducted individually or in combination at a part of the DNA sequence of sequence ID NO 2. Further, use may be made of one chemically synthesized.

The obtained recombinant expression vector is introduced into a host in accordance with any of the competent cell method [see J. Mol. Biol., Vol.53, p.154 (1970)], the protoplast method [see Proc. Natl. Acad. Sci. USA, Vol.75, p.1929 (1978)], the calcium phosphate method [see Science, Vol.221, p.551 (1983)], the in vitro packaging method [see Proc. Natl. Acad. Sci. USA, Vol.72, p.581 (1975)], the virus vector method [see Cell, Vol.37, p.1053 (1984)], etc., thereby preparing a transformant. Any of *Escherichia coli*, *Bacillus subtilis*, yeast, insect cells, animal cells and the like is used as the host. The obtained transformant is cultured in a medium suitable for the host. The culturing is generally conducted at 20° to 45° C. and at pH of 5 to 8, in which aeration and agitation are executed according to necessity. The separation of the RPDL protein from the resultant culture and its purification may be conducted by an appropriate combination of conventional separation and purification methods. Examples of these conventional methods include salting out, solvent precipitation, dialysis, gel filtration, electrophoresis, ion exchange chromatography, affinity chromatography, and reversed-phase high-performance liquid chromatography.

(8) Preparation of antibody

Antibodies can be prepared by the conventional method in which the whole or a part of the RPDL protein is used as an antigen. For example, a polyclonal antibody can be prepared by giving a plurality of subcutaneous, intramuscular, intraperitoneal or intravenous inoculations of the antigen to an animal such as a mouse, a guinea-pig and a rabbit to thereby satisfactorily immunize the same, collecting the blood specimen from the animal, and performing serum separation. In this procedure, commercially available adjuvants can be used.

A monoclonal antibody can be prepared by, for example, conducting the fusion of splenocytes of a mouse immunized with the RPDL protein with commercially available mouse myeloma cells to thereby prepare a hybridoma and either culturing the hybridoma followed by separation of the antibody from the resultant supernatant or administering the hybridoma to a mouse followed by separation of the antibody from the mouse ascites.

The RPDL protein as an antigen does not necessarily have to possess the whole amino acid structure and use may be made of a peptide having a partial structure of the protein, a variant or derivative of the protein, or a fusion peptide resulting from the fusion with another peptide. The method for preparing these is not critical and it may be biological or chemosynthetic.

The obtained antibody enables the identification and quantity determination of RPDL protein in human biospecimens and can be used in, for example, various agents.

The immunoassay of RPDL protein may be conducted in accordance with the generally known procedure and can be executed by, for example, any of the fluorescent antibody technique, passive agglutination and enzyme antibody technique.

(4) Analyses of mutation and abnormality of gene

Any mutation of a gene encoding the RPDL protein can be analyzed by the use of a probe comprising a restriction enzyme fragment of the DNA provided by the present invention or by the use of, as a primer, an oligonucleotide obtained by appropriately selecting a suitably positioned nucleotide sequence from the DNA and synthesizing therewith.

Also, any abnormality such as insertion and deletion in the gene of a specimen can be detected by the above analysis.

The *Escherichia coli* L1-3977 carrying the plasmid containing the DNA encoding the above RPDL protein was deposited with National Institute of Bioscience and Human-Technology, Agency of Industrial Science and Technology, Ministry of International Trade and Industry under the accession number FERM BP-4805 on Sep. 21, 1994.

The use of a substance including the whole or a part of each of the human RPDL protein and the DNA encoding the protein according to the present invention has enabled analyses on the level of human cells not only of the functions of the above protein as a transcriptional control factor and the gene per se but also of the effects of any variation of the above protein. It is apparent that the protein of the present invention is an important transcriptional control protein commonly acting on many target genes and having both functions of activation and inactivation from the viewpoint of the homology of its amino acid sequence with that of the yeast RPD3. The contribution of the above investigations to the elucidation of the fundamental working of human cells, such as differentiation, amplification, activity and life and death thereof, is being anticipated. Moreover, the sequence structure of the above gene and its location on the chromosome have been defined, so that it can be anticipated that its relationships with not only tumors but also other various diseases and abnormalities of the gene are elucidated and its application is found in the pharmaceutical field.

EXAMPLES

The present invention will be concretely described in detail with reference to the following Examples which in no way limit the scope of the invention.

Example 1

Preparation of human fetal lung cDNA library cDNA was synthesized on the basis of mRNA derived from human fetal lung tissue (purchased from Clontech) and a cDNA library containing cloned cDNA inserts in a given direction was prepared by the use of UniZAPxR vector kit (purchased from Stratagene).

Example 2

Selection of clone

The nucleotide sequence of each of 2058 clones of the cDNA library prepared in Example 1 was partially determined from the 5'-terminal side. The resultant nucleotide sequences were compared with the known nucleotide sequences of a data base to find out one clone L1-3977 having homology with the yeast RPD3. A partial sequence (258 bp) of the clone L1-3977 exhibited a homology of 60.2% with the RPD3 gene (Accession No. S66438, 1645 bp) of yeast (*Saccharomyces cerevisiae*) in the range of 176 bp.

Example 3

Sequencing of full-length cDNA and characteristics of structure

The DNA sequence of the clone L1-3977 obtained in Example 2 was determined by the Dideoxy method [see F. Sanger et al., Proc. Natl. Acad. Sci. USA, Vol.74, p.p.5463–5467 (1977)]. As a result, it was found that the clone L1-3977 contained a full-length cDNA having a novel sequence specified in sequence ID NO 2. The amino acid sequence of a novel protein (sequence ID NO 1, RPDL protein) composed of 482 amino acid residues was deduced from an open reading frame formed of 64th to 1509th nucleotides of the above DNA sequence.

This amino acid sequence exhibited a homology of 60.0% with the RPD3 protein (Accession No. 22284 & P32561, 433 amino acid residues) of yeast (*S. cerevisiae*) in the range of 422 amino acid residues.

The nucleotide sequence of sequence ID NO 2 (2111 bp) exhibited a homology of 62.1% with the RPD3 gene (Accession No. S66438, 1645 bp) of yeast (*S. cerevisiae*) in the range of 1168 bp. Further, it exhibited a homology as high as 80.94 with the RPD3 homologue gene (Accession No. X78454, 1040 bp) of *Xenopus laevis* in the range of 1034 bp. A homology as high as 94.84 was recognized in the range of 343 amino acid residues between the protein (343 amino acid residues) encoded by the RPD3 homologue gene (Accession No. X78454, 1040 bp) of *Xenopus laevis* and the RPDL protein of the present invention.

The above homology data demonstrate that the RPDL protein of the present invention is an important human transcriptional control protein having the same functions as those of the RPD3 protein of a yeast. In addition, the nucleotide sequence (2111 bp) of sequence ID NO 2 has exhibited a homology as high as 78.9% with the nucleotide sequence of the 3'-noncoding region of proto-oncogene c-tk1 (chicken tyrosine kinase proto-oncogene) in a range as wide as 1534 bp, so that the importance of the RPDL protein of the present invention in the transcriptional control mechanism has also been supported from the recent information on the association of the gene 3'-noncoding region with the control of transcription and translation.

Example 4

Analysis of expression in various human tissues

Expression analysis by Northern blot system (purchased from Clontech) was conducted with respect to various human tissue mRNAs with the use of the cDNA obtained in Example 3 as a probe. The conditions recommended by the manufacturer were obeyed on hybridization and washing, and autoradiography was conducted at –80° C. for 16 hours. Actin was used as a control. As a result, expression was recognized in the form of a mRNA band having a size of about 2.4 kbp in all the studied tissues (heart, kidney, liver, lung, pancreas, placenta, skeletal muscle, large intestine, peripheral leukocyte, ovary, prostate, small intestine, spleen, testis, and thymus gland) except the brain. While expression scarcely occurred in the brain, relatively strong expression occurred in the heart, pancreas and testis and relatively weak expression in the kidney.

Example 5

Chromosome mapping of the gene

The cDNA obtained in Example 3 was used as a probe for investigating the location of the gene encoding the RPDL protein of the present invention on the chromosome. That is, the location on the chromosome with which the above probe hybridized was determined by the FISH method [see Inazawa et al., Genomics, Vol.10, p.p.1075–1078 (1991)]. As a result, the location was identified as being at 1p34.1 on the short arm of chromosome 1. This location was the one at which deletion was recognized in mammary carcinoma [see A. Borg et al., Genes Chromosome Cancer, Vol.5, p.p.311–320 (1992)] and gastric carcinoma [see T. Sano et al., Cancer Res., Vol.51, p.p.2926–2931 (1991)].

Example 6

Construction of recombinant RPDL protein expression vector

A partial sequence including the protein coding region was amplified by PCR with the use of the cDNA obtained in Example 3 as a template. BamHI and EcoRI cleavage sites were added to the 5'-terminus of one primer and the 5'-terminus of the other primer, respectively. The obtained amplification product was digested with BamHI and EcoRI. The resultant fragment was inserted into expression vector pGEX-2T (purchased from Pharmacia) preliminaly digested with BamHI and EcoRI, thereby constructing expression plasmid pGST-RPDL. *E. coli* DH5α was transformed with the plasmid pGST-RPDL and the resulting transformants were selected based on ampicillin resistance, thereby obtaining a transformant capable of expressing a fusion protein of glutathione-S-transferase and RPDL protein.

Example 7

Expression of recombinant RPDL protein and its purification

The transformant obtained in Example 6 was cultured, and a recombinant RPDL fusion protein was extracted from the resultant culture and purified.

Specifically, the transformant was cultured by shaking the same in 100 ml of LB medium (1% peptone, 0.54 yeast extract and 1% NaCl) at 37° C. overnight. The resultant liquid culture was diluted tenfold with LB medium preliminary heated to 37° C. and the resulting dilution was further cultured at 37° C. for 30 to 90 minutes, thereby obtaining a culture of logarithmic growth phase. Isopropyl β-D-thiogalactopyranoside was added to 1 l of the culture so that the final concentration thereof was 1 mM, followed by culturing for 3 to 4 hours. The culture was centrifuged to thereby separate bacterial cells. 10 ml of a column buffer (150 mM NaCl, 16 mM $Na_2HPO_4$, 4 mM $NaH_2PO_4$, pH 7.3) was added to bacterial cells transformed with the expression vector pGST-RPDL, followed by sonication. A soluble fraction of a supernatant resulting from the cell disruption was applied to a glutathione-Sepharose 4B column (purchased from Pharmacia). The column was washed with the column buffer and then elution was conducted with an eluent containing 5 mM reduced glutathione. The eluted fraction was analyzed and fractionated by SDS polyacrylamide electrophoresis. As a result, a fraction in which the desired GST fusion protein of about 80 kDa was detected as a main band was obtained from the transformant constructed with the plasmid pGST-RPDL.

---

What we claim is:

1. A protein having the amino acid sequence specified in sequence ID NO 1.

2. A polyclonal antibody or a monoclonal antibody capable of binding with a protein having the amino acid sequence specified in sequence ID NO 1.

* * * * *